United States Patent [19]

Hermecz et al.

[11] Patent Number: 4,981,966
[45] Date of Patent: Jan. 1, 1991

[54] PROCESS FOR THE PREPARATION OF QUINOLINE CARBOXYLIC ACIDS

[75] Inventors: István Hermecz; Géza Kereszturi; Lelle Vasvári née Debreczy; Ágnes Horváth, all of Budapest; Mária Balogh, Dunakeszi; Gábor Kovács, Budapest; Tamás Szûts, Budapest; Péter Ritli, Budapest; Judit Sipos, Budapest; Anikó Pajor, Budapest, all of, Hungary

[73] Assignee: Chinoin Gyogyszer Es Vegyeszeti Termekek Gyara Rt., Budapest, Hungary

[21] Appl. No.: 295,439

[22] Filed: Jan. 10, 1989

Related U.S. Application Data

[62] Division of Ser. No. 104,053, Oct. 8, 1987, abandoned.

[30] Foreign Application Priority Data

| Dec. 9, 1985 [HU] | Hungary | 4694/85 |
| Dec. 9, 1985 [HU] | Hungary | 4695/85 |
| Dec. 9, 1986 [HU] | Hungary | PCT/HU86/00069 |

[51] Int. Cl.$^5$ .......................................... C07D 241/04
[52] U.S. Cl. ................................ 544/229; 544/363; 546/13
[58] Field of Search ................................ 544/229, 363

[56] References Cited

U.S. PATENT DOCUMENTS

| 4,528,287 | 7/1985 | Itoh et al. ............................ 544/363 |
| 4,806,645 | 2/1989 | Hermecz et al. ...................... 546/13 |

FOREIGN PATENT DOCUMENTS

| 0090424 | 10/1983 | European Pat. Off. ............ 544/363 |
| 0080683 | 5/1984 | Japan .................................. 544/229 |
| 58-184817 | 4/1985 | Japan . |
| 60-78986 | 5/1985 | Japan . |

OTHER PUBLICATIONS

"Chemical Abstracts", vol. 103, 1985, Col. 103:123491p. (Abstract of Japanese Patent No. 60-78,986, pub. 5/4/85).
"Chemical Abstracts", vol. 105, 1986, Col. 105:153293j, (Abstract of Japanese Patent No. 60-75,489, pub. 4/27/85).

*Primary Examiner*—Richard L. Raymond
*Assistant Examiner*—James H. Turnipseed
*Attorney, Agent, or Firm*—Herbert Dubno; Jonathan Myers

[57] ABSTRACT

The invention relates to a new process for the preparation of compounds of the Formula I

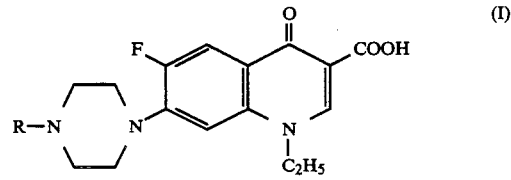

(wherein R stands for hydrogen or methyl) and pharmaceutically acceptable salts thereof which comprises reacting a compound of the Formula V

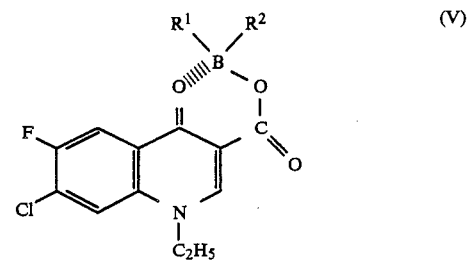

(wherein $R^1$ and $R^2$ stand for an aliphatic acyloxy group comprising 2-6 carbon atoms and optionally substituted by halogen; or for an aromatic acyloxy group comprising 7-11 carbon atoms) with an amine of the Formula VI

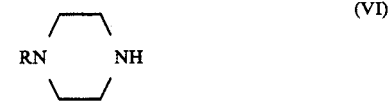

(wherein R has the same meaning as stated above) or a salt thereof and subjecting the compound of the Formula VII

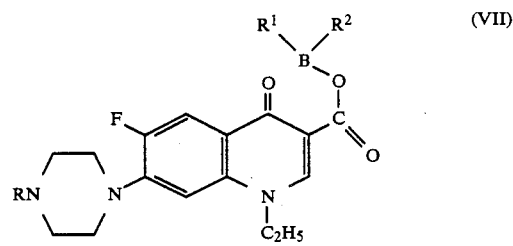

thus obtained (wherein R, $R^1$ and $R^2$ are as stated above) to hydrolysis after or without isolation and if desired converting the compound of the Formula I thus obtained into a salt thereof or setting free the same from its salt.

The compounds of the Formula I are known antibacterial agents.

The advantage of the process of the present invention is that it makes the desired compounds of the Formula I available in a simple manner, with high yields and in a short reaction time.

4 Claims, No Drawings

PROCESS FOR THE PREPARATION OF QUINOLINE CARBOXYLIC ACIDS

CROSS REFERENCE TO RELATED APPLICATIONS

This application is a divisional application of U.S. patent application Ser. No. 104,053 filed 8 Oct. 1987, now abandoned which is a national phase application of PCT/HU86/00069 filed 9 Dec. 1986 and based upon Hungarian national application Nos. 4694/85 and 4695/95 filed 9 Dec. 1985 under the International Convention. It is also related to the concurrently filed, commonly owned copending patent application Ser. No. 105,295 filed 7 Apr. 1987 now U.S. Pat. No. 4,806,645.

This invention relates to a new process for the preparation of 1-ethyl-6-fluor-7-(4-optionally substituted piperazino)-4-oxo-1,4-dihydro-quinoline-3-carboxylic acid derivatives and pharmaceutically acceptable salts thereof.

It is known that the quinoline carboxylic acid derivatives of the Formula I

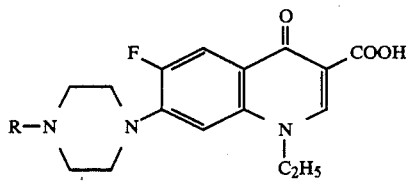

are widespreadly used due to their high antibacterial activity for the treatment of diseases of the urinary tract and those of systemic bacterial origin (J. Pharm. Sci. 1984, 73, 1379; Eur. J. Chemother. Antibiot. 1983, 3, pages 9 and 47; J. Antimicrob. Chemother. 1984, 13, Suppl., 99, pages 107 and 113).

In the Formula I, R stands for hydrogen or methyl.

The quinoline-carboxylic acid of the Formula I (wherein R stands for hydrogen) can be prepared by reacting 1-ethyl-6-fluoro-7-chloro-4-oxo-1,4-dihydro-quinoline-3-carboxylic acid and piperazine (Belgian patent specification Nos. 863,429 and 870,576; Japanese patent specification No. 80 33,543 and J. Med. Chem. 23, 1358, (1980) or by subjecting ethyl-1-ethyl-6-fluoro-7-piperazino-4-oxo-1,4-dihydro-quinoline-3-carboxylate of the Formula III

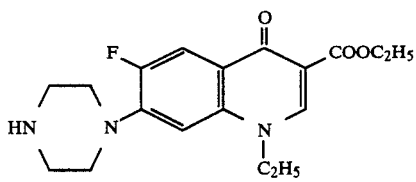

to hydrolysis (Belgian patent specification Nos. 879,106 and 890,223).

The common disadvantage of the above processes is that the exchange reaction of the chlorine atom in position 7 to piperazine is carried out under vigorous reaction conditions, at a temperature of 115°–175° C., for 5–19 hours, optionally even under pressure. Moreover the reaction is not regioselective and under the above reaction conditions the fluorine atom in position 6 partially reacts with piperazine (J. Med. Chem. 23, 1358, (1980).

The quinoline carboxylic acid of the Formula I, wherein R stands for methyl, may be prepared by reacting 1-ethyl-6-fluoro-7-chloro-4-oxo-1,4-dihydro-quinoline-3-carboxylic acid of the Formula II

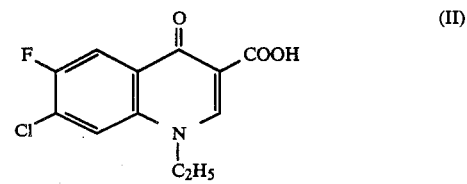

with 1-methyl-piperazine (Belgian patent Nos. 870,576 and 870,917; Laid-open Japanese patent application No. 80 33,453 and J. Med. Chem. 23, 1358 (1980) or by methylating 1-ethyl-6-fluoro-7-piperazino-4-oxo-1,4-dihydro-quinoline-3-carboxylic acid of the Formula IV

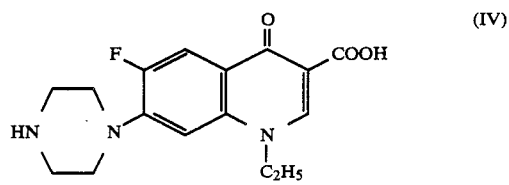

(Belgian patent No. 870,917 and FR-OS No. 2,424,919). The common disadvantage of the these processes is that the reactions are carried out under vigorous and agressive reaction conditions, at a temperature between 110° and 150° C., during 7–16 hours. The yields vary between 55% and 66%. Moreover the reaction mixture is worked up in a complicated manner.

According to the present invention there is provided a new process for the preparation of compounds of the Formula I (wherein R stands for hydrogen or methyl) and pharmaceutically acceptable salts thereof, which comprises reacting a compound of the Formula V

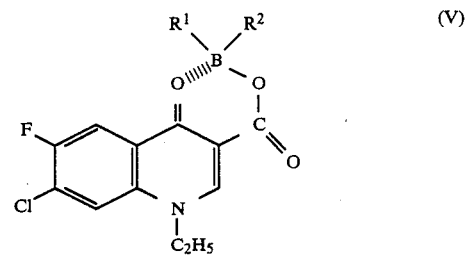

(wherein $R^1$ and $R^2$ stand for an aliphatic acyloxy group comprising 2–6 carbon atoms and optionally substituted by halogen; or for an aromatic acyloxy group comprising 7–11 carbon atoms) with an amine of the Formula VI

(wherein R has the same meaning as stated above) or a salt thereof and subjecting the compound of the Formula VII

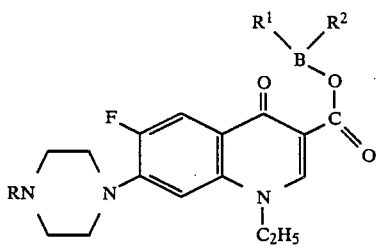

(VII)

thus obtained (wherein R, $R^1$ and $R^2$ are as stated above) to hydrolysis after or without isolation and if desired converting the compound of the Formula I thus obtained into a salt thereof or setting free the same from its salt.

The advantage of the process of the present invention is that it enables the preparation of the compounds of the Formula I in a simple manner, with very high yields and in a short reaction time.

In the Formula V $R^1$ and $R^2$ may be the same or different.

The borate derivatives of the Formulae V and VII are new compounds.

According to a preferred form of realization of the process of the present invention the borate derivative of the Formula VII is converted into the desired quinoline-3-carboxylic acid of the Formula I without isolation.

The borate derivatives of the Formula V can be reacted with the amine of the Formula VI if desired in the presence of an inert organic solvent and an acid binding agent.

As inert organic solvent preferably an acid amide (e.g. dimethyl formamide, dimethyl acetamide), a ketone (e.g. acetone, methyl ethyl ketone), an ether (e.g. dioxane, tetrahydrofuran, diethyl ether), an ester (e.g. ethyl acetate, methyl acetate, ethyl propionate), a sulfoxide (e.g. dimethyl sulfoxide), an alcohol (e.g. methanol, ethanol, 1-decanol, butanol) may be used.

As acid binding agent an organic or inorganic base may be used. From the group of organic bases trialkyl amines (e.g. triethyl amine, tributyl amine), cyclic amines (e.g. pyridine, 1,5-diazabicyclo(5.4.0)undec-5-ene, 1,5-diazabicyclo(4.3.0)non-5-ene, 1,4-diazabicyclo(2.2.2)octane) can be mentioned, while as inorganic base preferably hydroxides or carbonates of alkali or alkaline earth metals can be applied. Thus as acid binding agent advantageously potassium carbonate, potassium hydrogen carbonate, sodium hydroxide, calcium hydroxide, etc. or an excess of the amine of the Formula VI can be used.

The borone derivative of the Formula V and the amine of the Formula VI can be reacted at a temperature between 0° and 200° C., depending on the solvent used. The reaction time may vary between half an hour and 10 hours. The reaction time depends on the reaction temperature, too. If the reaction is carried out at higher temperature, the reaction time can be shortened. The above reaction conditions are but preferable values and other conditions may be used as well.

The borates of the Formula VII can be hydrolyzed to the desired quinoline-3-carboxylic acids of the Formula I, after or without isolation, under acidic or basic conditions. The compound of the Formula VII precipitates from the reaction mixture e.g. on cooling and can be separated e.g. by filtration or centrifuging, if desired.

Basic hydrolysis may be preferably carried out with the aid of a hydroxide or carbonate of an alkali metal or an alkaline earth metal hydroxide, used as aqueous solution. One may preferably use an aqueous solution of sodium hydroxide, potassium hydroxide, sodium carbonate, potassium hydrogen carbonate, potassium carbonate, calcium hydroxide. However, organic amines (e.g. triethyl amine) may also be applied in the hydrolysis step.

Acidic hydrolysis may preferably be accomplished by using an aqueous mineral acid. One may preferably proceed by hydrolysing a borate of the Formula VII by heating with an aqueous solution of hydrochloric acid, hydrogen bromide, sulfuric acid or phosphoric acid. Hydrolysis may also be accomplished with the aid of an organic acid (e.g. acetic acid, propionic acid, etc.).

Hydrolysis of the compounds of the Formula VII may also be carried out in aqueous medium in the presence of a water-miscible organic solvent. For this purpose e.g. alcohols (e.g. methanol, ethanol), a ketone (e.g. acetone), an ether (e.g. dioxane), an acid amide (e.g. dimethyl formamide), a sulfoxide (e.g. dimethyl sulfoxide), or pyridine may be used.

The quinoline-3-carboxylic acid of the Formula I thus obtained may be isolated e.g. by adjusting the pH value of the aqueous solution to a suitable value and separating the precipitated crystals e.g. by filtration or centrifuging by liophylizing the aqueous reaction mixture.

The compounds of the Formula I can be converted into pharmaceutically acceptable salts thereof in a known manner. Thus preferably acid addition salts can be formed, e.g. salts formed with hydrogen halides, sulfonic acids, sulfuric acid or organic acids. One may form preferably the chlorides, bromides, aryl sulfonates, methane sulfonates, maleates, fumarates, benzoates, etc. The compounds of the Formula I form salts with alkali or alkaline earth metals or other metal ions as well. Accordingly the sodium, potassium, magnesium, iron, copper salts, etc. may be prepared.

The compounds of the Formula I and pharmaceutically acceptable salts thereof can be converted into the hydrates (e.g. hemihydrates, trihydrates, etc.) by methods known per se.

According to a further aspect of the present invention there are provided new compounds of the Formula VII (wherein R, $R^1$ and $R^2$ are as stated above).

The starting materials of the Formula V can be prepared by reacting 1-ethyl-6-fluoro-7-chloro-4-oxo-1,4-dihydro-quinoline-3-carboxilatic acid of the Formula II (Belgian patent No. 863,429) with a borone derivative (e.g. with a compound of the Formula VIII

(VIII)

wherein $R^3$, $R^4$ and $R^5$ stand for an alkyl group having 1–5 carbon atoms and optionally substituted by halogen or an aryl group comprising 6–10 carbon atoms) optionally in an organic medium.

Further details of the present invention are to be found in the following Examples without limiting the scope of protection to the said Examples.

EXAMPLE 1

19.5 g of 1-ethyl-6-fluoro-7-chloro-4-oxo-1,4-dihydro-quinoline-3-carboxylic acid-borone-di(propionyloxy)-anhydride and 11.9 g of piperazine are reacted in 72 ml of dimethyl sulfoxide at 110° C. for an hour. The reaction mixture is cooled to 90° C. and 116 ml of a 6 weight/vol % aqueous sodium hydroxide solution are added. The aqueous reaction mixture is kept for an hour under slight boiling whereupon it is cooled to room temperature. The pH value of the solution is adjusted to 7 with 96 weight/vol % acetic acid. The reaction mixture is allowed to crystallize in a refrigerator overnight. Next morning the precipitated crystals are filtered, washed with water and dried in vacuo at 90°–95° C. until constant weight. Thus 14.0 g of 1-ethyl-6-fluoro-4-oxo-1,4-dihydro-7-piperazino-quinoline-3-carboxylic acid are obtained, yield 95.9%. The product decomposes at 221°–222° C. (from a mixture of dichloro methane and methanol).

Analysis for the Formula $C_{16}H_{18}FN_3O_3$ calculated C=60.18%, H=5.68%, N=13.16%; found C=60.07%, H=5.74%, N=13.18%.

The starting material is prepared as follows:

A mixture of 9.3 g of boric acid and 70 g of propionic anhydride is stirred at 100° C. for 15 minutes, whereupon the reaction mixture is heated to the boiling point. After half an hour the temperature is lowered to 110° C. and 29.8 g of ethyl-1-ethyl-6-fluoro-7-chloro-4-oxo-1,4-dihydro-quinoline-3-carboxylate are added. The reaction mixture, which turns into a thick suspension within some minutes, is stirred at 110° C. for 2 hours, cooled to room temperature and diluted with 300 ml of water. The reaction mixture is cooled and the precipitated crystals are filtered. Thus 41.5 g of 1-ethyl-6-fluoro-7-chloro-4-oxo-1,4-dihydro-quinoline-3-carboxylic acid-borone-di(propionyloxy)-anhydride are obtained, yield 97.7%. The product decomposes at 252° C.

Analysis for the Formula $C_{18}H_{18}BFClNO_7$ calculated C=50.79%, H=4.26%, N=4.29%. found C=50.94%, H=4.15%, N=3.41%.

EXAMPLE 2

19.5 g of 1-ethyl-6-fluoro-7-chloro-4-oxo-1,4-dihydro-quinoline-3-carboxylic acid-borone-di(propionyloxy)-anhydride and 13.3 g of 4-methyl-piperazine are reacted in 72 ml of dimethyl sulfoxide at 110° C. for 2 hours. The reaction mixture is cooled to 90° C. and 116 ml of a 6 weight/vol % aqueous sodium hydroxide solution are added. The aqueous reaction mixture is kept for an hour under slight boiling and cooled to room temperature. The pH value of the solution is adjusted to 7 with a 96 weight/vol % acetic acid. The reaction mixture is allowed to crystallize in a refrigerator, after 5 hours the precipitated crystals are filtered, washed with water and dried at 85° C. in vacuo until constant weight. Thus 13.9 g of 1-ethyl-6-fluoro-7-(4-methyl-piperazino)-4-oxo-1,4-dihydro-quinoline-3-carboxylic acid are obtained, yield 269°–271° C. (The product decomposes at 269°–271° C. from a mixture of dimethyl formamide and methanol.)

Analysis for the Formula $C_{17}H_{20}FN_3O_3$ calculated C=61.25%, H=6.05%, N=12.60%; found C=61.37%, H=5.91%, N=12.47%.

2 g of 1-ethyl-6-fluoro-7-(4-methyl-piperazino)-4-oxo-1,4-dihydro-quinoline-3-carboxylic acid are heated in 30 ml of anhydrous ethanol to boiling and to the boiling solution 0.61 g of methanesulfonic acid are added. From the solution thus obtained the precipitation of crystals begins within some minutes. After 10 minutes the reaction mixture is cooled to 0° C. and allowed to crystallize in a refrigerator overnight. Next day the precipitated crystals are filtered, washed with ethanol and dried in vacuo at 90°–95° C. until constant weight. Thus 2.3 g of the methanesulfonic acid salt of 1-ethyl-6-fluoro-7-(4-methyl-1-piperazino)-4-oxo-1,4-dihydro-quinoline-3-carboxylic acid are obtained, yield 89.3%. The product decomposes at 285°–287° C.

Analysis for the Formula $C_{18}H_{24}FN_3O_6S$ calculated C=50.34%, H=5.63%, N=9.78%; found C=50.12%, H=5.81%, N=9.79%.

The starting material may be prepared as follows:

A mixture of 9.3 g of boric acid and 70 g of propionic anhydride is stirred at 100° C. for 15 minutes whereupon the temperature is raised to the boiling point. After half an hour the temperature is lowered to 110° C. and 29.8 g of ethyl-1-ethyl-6-fluoro-7-chloro-4-oxo-1,4-dihydro-quinoline-3-carboxylate are added. The reaction mixture, which turns into a thick suspension within some minutes, is heated at 110° C. for 2 hours, cooled to room temperature and diluted with 300 ml of water. The reaction mixture is cooled and the precipitated crystals are filtered. Thus 41.5 g of 1-ethyl-6-fluoro-7-chloro-4-oxo-1,4-dihydro-quinoline-3-carboxylic acid-borone-di(propionyloxy)-anhydride are obtained, yield 97.7%. The product decomposes at 252° C.

Analysis for the Formula $C_{18}H_{18}BFClNO_7$ calculated C=50.79%, H=4.26%, N=3.29%; found C=50.94%, H=4.15%, N=3.41%.

EXAMPLE 3

19.9 g of (1-ethyl-6-fluoro-7-chloro-4-oxo-1,4-dihydro-quinoline-3-carboxylate-$O^3,O^4$)-bis(acetate-O)-boron and 15.0 g of 1-methyl piperazine are reacted in 100 ml dimethylsulfoxide at 110°–115° C. for 2 hours.

The reaction mixture is then allowed to cool to 80°–90° C. and 126 ml of a 6% by W/V aqueous solution of sodium hydroxide are added. The reaction mixture is mildly boiled for 1.5 hours, whereafter active charcoal is added and filtered. After cooling to room temperature the pH of the solution is adjusted to 6.5 by adding 96% by W/V acetic acid. The reaction mixture is kept at 0° C. for half day, whereafter the precipitated crystals are filtered and washed with water and methanol. Thus 14.3 g (85.8%) of 1-ethyl-6-fluoro-7-(4-methyl-piperazino)-4-oxo-1,4-dihydro-quinoline-3-carboxylic acid are obtained.

Decomposition at 268°–270° C. (from a mixture of dimethylformamide and methanol). No depression of melting point is obtained when admixing the product with the compound obtained according to Example 2.

The preparation of the starting material:

9.3 g of boric acid and 54.1 g of acetic acid anhydride (95%) are admixed and slowly heated and kept at 100° C. for 30 minutes. 29.8 g of ethyl-(1-ethyl-6-fluoro-7-chloro-4-oxo-1,4-dihydro-quinoline-3-carboxylate are then added to the reaction mixture. Within some minutes the first crystals are precipitated, the suspension paste is stirred for 2 hours and cooled to 10° C. and 100 ml of cold water are added and the precipitated crystals are filtered. Thus 38.7 g. (97.5%) of (1-ethyl-6-fluoro-7-chloro-4-oxo-1,4-dihydro-3-quinoline-carboxylate-$O^3,O^4$)-bis(acetate-O)-boron are obtained, decomposing at 278° C.

Analysis for the formula $C_{16}H_{14}BClFNO_7$ calculated: C=48.35% H=3.55% N=3.52% found: C=48.49% H=3.46% N=3.71%.

EXAMPLE 4

3.97 g. of (1-ethyl-6-fluoro-7-chloro-4-oxo-1,4-dihydro-quinoline-3-carboxylate-$O^3,O^4$)-bis-(acetate-O)-boron and 3.00 g. of 1-methyl-piperazine are reacted in 40 ml of dimethylsulfoxide for 250 hours at 25° C. To the reaction mixture 20 ml of an aqueous solution of 6% by W/V sodium hydroxide are added and the reaction temperature is raised to 110° C. within 30 minutes. The mixture is mildly boiled for a further half hour, it is filtered warm and cooled. The pH of the solution is adjusted to 7 by adding 96% by W/V acetic acid. The reaction mixture is allowed to crystallize overnight in a refrigerator and the precipitated crystals are filtered and washed with some water, and beige crystals are obtained (2.8 g, 84%). After recrystallization from a mixture of dimethylformamide and methanol 1-ethyl-6-fluoro-4-oxo-7-(1-methyl-piperazino)-1,4-dihydro-quinoline-3-carboxylic acid is obtained, decomposing at 267°-269° C. after drying to constant weight at 90°-95° C. in vacuo. No melting point depression is obtained when admixed with the product of Example 2 at any ratio.

EXAMPLE 5

7.95 g (1-ethyl-6-fluoro-7-chloro-4-oxo-1,4-dihydro-3-quinoline-carboxylate-$O^3,O^4$)-bis(acetate-O)-boron and 5.17 g. of piperazine are reacted at 110° C. for 1 hour in 30 ml. of dimethylsulfoxide. The reaction mixture is then cooled to 90° C. and an aqueous solution of 6% by W/V sodium hydroxide (30 ml.) is added and the mixture is heated to 110° C. within half hour and a further half hour stirred at this temperature. The mixture is filtered hot, then cooled to room temperature and then the pH is adjusted to 6.5 by adding 96% by W/V acetic acid. The product is allowed to stand for 1 day and the precipitated crystals are filtered and washed with water. 1-Ethyl-6-fluoro-7-piperazino-4-oxo-1,4-dihydro-quinoline-3-3-carboxylic acid is obtained (4.2 g, 66%), which does not show any depression of melting point when admixed with the product of Example 1.

EXAMPLE 6

3.97 g. (1-ethyl-6-fluoro-7-chloro-4-oxo-1,4-dihydro-quinoline-3-carboxylate-$O^3,O^4$)-bis(acetate-O)-boron are reacted with 2.58 g. of piperazine in 20 ml of dimethylsulfoxide for 180 hours at 25° C. To the reaction mixture an aqueous solution of 6% by W/V sodium hydroxide (20 ml) is added and the reaction temperature is raised to 110° C. within a half hour. The mixture is then mildly boiled for another 30 minutes, filtered hot and cooled. The pH of the solution is adjusted to 7 with 96% by W/V acetic acid. The reaction mixture is allowed to crystallize overnight in a refrigerator and the precipitated crystals are filtered, washed with water and pale beige crystals are obtained (3.0 g, 94%). After recrystallization form dichloromethane-methanol 1-ethyl-6-fluoro-4-oxo-7-piperazino-1,4-dihydro-quinoline-3-carboxylic acid is obtained, melting at 220°-222° C. after drying to constant weight at 90°-95° C. in vacuo. No depression of melting point is observed when admixing the product at any ratio with a substance prepared according to Example 1.

EXAMPLE 7

2.0 g of (1-ethyl-6-fluoro-7-chloro-4-oxo-1,4-dihydro-3-quinoline carboxylate-$O^3,O^4$)-bis(acetate-O)-boron and 1.3 g of piperazine are heated under reflux in 40 ml. of abs. methanol for 10 days on a waterbath. To the reaction mixture 12 ml. of an aqueous solution of 6% by W/V sodium hydroxide are added and heated under reflux for 2 hours. After cooling the mixture to room temperature the pH of the solution is adjusted to 6.5 by adding 96% by W/V acetic acid and the precipitated yellow crystals are filtered. The obtained 1-ethyl-6-fluoro-4-oxo-7-piperazino-1,4-dihydro-quinoline-3-carboxylic acid (1.55 g. 97%) is recrystallized from a mixture of dichloromethane and methanol, melting point: 220°-222° C. No depression of the melting point is obtained when admixing the product with the product of Example 1.

What we claim is:

1. A compound of the Formula (VII)

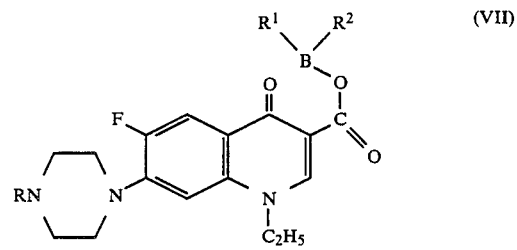

wherein
$R^1$ and $R^2$ are each $C_2$ to $C_6$ aliphatic acyloxy unsubstituted or substituted by halogen, or are each $C_7$ to $C_{11}$ aromatic acyloxy; and
R is hydrogen or methyl.

2. The compound of the Formula (VII) defined in claim 1 wherein R is hydrogen.

3. The compound of the Formula (VII) defined in claim 1 wherein R is methyl.

4. The compound of the Formula (VII) defined in claim 1 wherein $R^1$ and $R^2$ are each acetoxy or propionyloxy.

* * * * *